United States Patent [19]

Shoyab et al.

[11] Patent Number: 5,011,777
[45] Date of Patent: Apr. 30, 1991

[54] VECTORS ENCODING BRAIN DERIVABLE POLYPEPTIDE FACTORS

[75] Inventors: Mohammed Shoyab, Seattle; Hans Marquardt, Mercer Island; George J. Todaro, Seattle, all of Wash.

[73] Assignee: Oncogen, Seattle, Wash.

[21] Appl. No.: 546,248

[22] Filed: Jun. 29, 1990

Related U.S. Application Data

[60] Division of Ser. No. 823,159, Jan. 27, 1986, Pat. No. 4,963,485, which is a continuation-in-part of Ser. No. 766,864, Aug. 15, 1985, Pat. No. 4,806,492, which is a continuation-in-part of Ser. No. 694,712, Jan. 25, 1985, Pat. No. 4,714,683.

[51] Int. Cl.$^5$ .............................................. C12N 15/09
[52] U.S. Cl. ............................. 435/172.3; 435/69.1; 436/547; 530/350; 530/387
[58] Field of Search ....................... 435/69.1, 172.3; 436/547; 530/350, 387

[56] References Cited

U.S. PATENT DOCUMENTS

| | | | |
|---|---|---|---|
| 4,428,875 | 1/1984 | DeBarbieri | 530/331 |
| 4,457,867 | 7/1984 | Ishida | 530/351 X |
| 4,529,594 | 7/1985 | Hayashi | 514/12 |
| 4,714,683 | 12/1987 | Shoyab | 436/547 |
| 4,806,492 | 2/1989 | Shoyab | 436/547 |

OTHER PUBLICATIONS

Redding et al., P.N.A.S., U.S.A., (1982), 79:7014–7018.
Letnansky, Bioscience Reports, (1982), 2:39–45.
Chen, Trends in Biochemical Science, (1982), 7:364–365.
Holley et al., P.N.A.S., U.S.A., (1980), 77:5989–5992.
Beall et al., Cancer Biochem. Biophys., (1979), 3:93–96.
Holley et al., Cell Biol. Intl. Reports, (1983), 7:141–147.
Alho et al., Science, (1985), 229:179–182.
Guidotti et al., P.N.A.S., U.S.A., (1983), 80:3531–3535.
Ferrero et al., Neuropharmacology, (1984), 23:1359–1362.
Costa et al., Biochemical Pharmacology, (1985), 34:3399–3403.
Sangameswaran et al., P.N.A.S., U.S.A., (1985), 82:5560–5564.
Guidotti, A. et al., Nature, (1978), 275:553–555.

*Primary Examiner*—Richard A. Schwartz
*Assistant Examiner*—John D. Ulm
*Attorney, Agent, or Firm*—Irell & Manell

[57] ABSTRACT

Novel polypeptides, polynucleotide sequences, DNA constructs and compositions are provided for the preparation and use of polypeptides associated with naturally occurring polypeptides found in brains. The low molecular weight polypeptides either are growth inhibitors for neoplastic cells without inhibiting normal cells or affect GABA-ergic transmission. The polypeptides find use in inhibiting neoplastic growth, modulating diazepam receptor response, and detecting receptors for the polypeptides. Antibodies are provided in conjunction with the polypeptides, which may be used together or separately for detecting the presence of the polypeptides.

6 Claims, 6 Drawing Sheets

```
              *   Pro Ala Ala Leu Trp Ser Pro Pro Pro
5'-GAGGAGCTGA    CCA GCT GCG CTT TGG AGT CCT CCT CCC

Phe Gly Asn Val Asp Pro Arg Leu Arg Ser       -1
    TTC GGG AAT GTT GAT CCG CGG CTG CGC TCC       67

Met Phe Gln Phe His Ala Gly Ser Trp Glu
    ATG TTT CAG TTT CAT GCA GGC TCC TGG GAA

Ser Trp Cys Cys Cys Cys Cys Leu Ile Pro       20
    AGC TGG TGC TGC TGC TGC TGC CTG ATT CCA      127

Gly Asp Arg Pro Trp Asp Arg Gly Arg Arg
    GGC GAC AGA CCT TGG GAC CGC GGC CGG CGC

Trp Arg Leu Glu Met Arg His Thr Arg Ser       40
    TGG CGG CTG GAG ATG CGG CAC ACG AGA TCC      187

Val His Glu Thr Arg Phe Glu Ala Ala Val
    GTT CAC GAA ACC CGG TTT GAG GCG GCT GTG

Lys Val Ile Gln Ser Leu Pro Lys Asn Gly       60
    AAG GTG ATA CAG AGC TTG CCG AAA AAT GGT      247

Ser Phe Gln Pro Thr Asn Glu Met Met Leu
    TCA TTC CAG CCA ACA AAT GAA ATG ATG CTC

Lys Phe Tyr Ser Phe Tyr Lys Gln Ala Thr       80
    AAG TTC TAT AGC TTC TAT AAG CAG GCA ACT      307

Glu Gly Pro Cys Lys Leu Ser Lys Pro Gly
    GAA GGA CCT TGT AAA CTG TCA AAG CCT GGC

Phe Trp Asp Pro Val Gly Arg Tyr Lys Trp      100
    TTC TGG GAT CCT GTT GGA AGA TAC AAA TGG      367

Asp Ala Trp Ser Ser Leu Gly Asp Met Thr
    GAT GCG TGG AGT TCT TTG GGT GAT ATG ACC

Lys Glu Glu Ala Met Ile Ala Tyr Val Glu      120
    AAA GAG GAA GCC ATG ATT GCT TAT GTT GAA      427

Glu Met Lys Lys Ile Leu Glu Thr Met Pro
    GAA ATG AAA AAG ATT CTT GAA ACT ATG CCG

Met Thr Glu Lys Val Glu Glu Leu Leu His      140
    ATG ACT GAA AAA GTT GAA GAA TTG CTA CAT      487

Val Ile Gly Pro Phe Tyr Glu Ile Val Glu
    GTC ATT GGT CCA TTT TAT GAA ATT GTA GAA
```

```
Asp Lys Lys Ser Gly Arg Ser Ser Asp Leu    160
GAC AAA AAA AGT GGC AGA AGT TCT GAT TTA    547

Thr Ser Val Arg Leu Glu Lys Ile Ser Lys
ACC TCA GTC CGA CTG GAG AAA ATC TCT AAA

Cys Leu Glu Asp Leu Gly Asn Val Leu Ala    180
TGC TTA GAA GAT CTT GGT AAT GTT CTA GCT    607

Ser Thr Pro Asn Ala Lys Thr Val Asn Gly
TCT ACT CCA AAT GCC AAA ACT GTT AAT GGT

Lys Ala Glu Ser Ser Asp Ser Gly Ala Glu    200
AAA GCT GAA AGC AGT GAT AGT GGA GCT GAA    667

Ser Glu Glu Glu Ala Ala Gln Glu Asp Pro
TCT GAG GAA GAA GCA GCC CAA GAA GAC CCG

Lys Arg Pro Glu Pro Arg Asp Ser Asp Lys    220
AAA AGA CCA GAA CCA CGT GAT AGC GAT AAG    727

Lys Met Met Lys Lys Ser Ala Asp His Lys
AAA ATG ATG AAG AAA TCT GCA GAC CAT AAG

Asn Leu Glu Ile Ile Val Thr Asp Gly Tyr    240
AAT TTG GAA ATC ATT GTC ACT AAT GGC TAT    787

Asp Lys Asp Ser Phe Val Gln Gly Val Gln
GAT AAA GAC AGC TTT GTG CAG GGC GTA CAG

Asn Ser Ile His Thr Ser Pro Ser Leu Asn    260
AAT AGC ATT CAT ACC AGT CCT TCC CTG AAT    847

Gly Arg Cys Thr Glu Glu Val Lys Ser Val
GGC CGA TGC ACT GAG GAA GTA AAA TCT GTA

Asp Glu Asn Leu Glu Gln Thr Gly Lys Thr    280
GAT GAA AAC TTG GAG CAA ACT GGA AAA ACT    907

Val Val Phe Val His Gln Asp Val Asn Ser
GTT GTC TTC GTT CAC CAA GAT GTA AAC AGT

Asp His Val Glu Asp Ile Ser Gly Ile Gln    300
GAT CAT GTT GAA GAT ATT TCA GGA ATT CAG    967

His Leu Thr Ser Asp Ser Asp Ser Glu Val
CAT TTG ACA AGT GAT TCA GAC AGT GAA GTT

Tyr Cys Asp Ser Met Glu Gln Phe Gly Gln    320
TAC TGT GAT TCC ATG GAG CAA TTT GGG CAA   1027

Glu Glu Ser Leu Asp Gly Phe Ile Ser Asn
GAA GAG TCT TTA GAC GGC TTT ATA TCA AAC
```

```
Asn Gly Pro Phe Ser Tyr Tyr Leu Gly Gly   340
AAT GGA CCA TTT TCC TAT TAC TTG GGT GGT  1087

Asn Pro Ser  Gln Pro Leu Glu Ser Ser Gly
AAT CCC AGT  CAA CCG TTG GAA AGT TCT GGT

Phe Pro Glu Ala Val Gln Gly Leu Pro Gly   360
TTT CCT GAA GCT GTT CAA GGA CTT CCT GGG  1147

Asn Gly Ser  Pro Glu Asp Met Gln Gly Ala
AAC GGC AGC  CCT GAG GAC ATG CAG GGC GCA

Val Val Glu Gly Lys Gly Glu Val Lys Arg   380
GTG GTT GAA GGC AAA GGT GAA GTA AAG CGT  1207

Gly Gly Glu Asp Gly Gly Ser Asn Ser Gly
GGG GGA GAG GAC GGC GGG AGT AAC AGT GGA

Ala Pro His Arg Glu Lys Arg Ala Gly Glu   400
GCC CCG CAC CGC GAG AAA CGG GCT GGA GAA  1267

Ser Glu Glu Phe Ser Asn Ile Arg Arg Gly
AGT GAG GAG TTC TCT AAC ATT AGG AGA GGG

Arg Gly His Arg Met Gln His Leu Ser Glu   420
AGA GGG CAC AGG ATG CAG CAT TTG AGT GAA  1327

Gly Ser Lys Gly Arg Gln Val Gly Ser Gly
GGA AGC AAG GGT CGG CAA GTG GGA AGT GGA

Gly Asp Gly Glu Arg Trp Gly Ser Asp Arg   440
GGT GAT GGG GAA CGC TGG GGT TCG GAC AGA  1387

Gly Ser Arg Gly Ser Leu Asn Glu Gln Ile
GGC TCA AGG GGC AGC CTG AAC GAG CAG ATC

Ala Leu Val Leu Met Arg Leu Gln Glu Asp   460
GCG CTT GTG CTC ATG CGC CTG CAG GAG GAC  1447

Met Gln Asn Val Leu Gln Arg Leu His Lys
ATG CAG AAC GTC CTC CAG AGA CTC CAC AAA

Leu Glu Met Leu Ala Ala Ser Gln Ala Lys   480
CTG GAG ATG CTG GCG GCA TCA CAG GCA AAA  1507

Ser Ser Ala Leu Gln Thr Ser Asn Gln Pro
TCA TCA GCA TTA CAG ACC AGT AAT CAG CCC

Thr Ser Pro Arg Pro Ser Trp Trp Pro Phe   500
ACT TCA CCG AGA CCA TCT TGG TGG CCC TTC  1567

Glu Met Ser Pro Gly Ala Leu Thr Phe Ala
GAG ATG TCT CCT GGT GCA TTA ACC TTC GCT
```

| Ile | Ile | Trp | Pro | Phe | Ile | Ala | Gln | Trp | Leu | 520 |
|-----|-----|-----|-----|-----|-----|-----|-----|-----|-----|-----|
| ATC | ATA | TGG | CCT | TTT | ATT | GCT | CAG | TGG | TTG | 1627 |

| Val | His | Leu | Tyr | Tyr | Gln | Arg | Arg | Arg | Arg |
|-----|-----|-----|-----|-----|-----|-----|-----|-----|-----|
| GTG | CAT | TTA | TAT | TAC | CAA | AGA | AGG | AGA | AGA |

Lys Leu Asn  *
AAA TTG AAC TAAAGAAAATGACATTTTGTTGAAGAA 1693

ATCTACTGGCCCTGGATAACCTCGGGATGATACCAATTG

TGGAGCTTACACGAGGGA-3'  1750

```
                    5'-GAGCACCGGTGGAGAGGCCTAAGGTTGCG               29

*   Val Ser Cys Ala                 -21
CTTCTAAAATCGCTGCCAGTTGA           GTC TCT TGT GCT                  64

Gly Ser Trp  -   -   -   -   -   Leu
Ala Ala Thr Phe Ser Ser Pro Pro Pro Arg                           -11
GCT GCT ACC TTC TCT TCG CCG CCT CCG CGG                            94
5'  -G- T-- -GG --C --- --T --- --- -T-

NaeI
                                             ↓
Ser Pro Trp Ser Ser  -  Lys Ser  -  Arg
Ala Ser Trp Asn Leu Cys Asn Thr Ala Gly                            -1
GCT TCC TGG AAT CTT TGC AAC ACC GCC GGC                           124
T-- C-- --- -G- TC- --- --G T-G --- A-G

-   -   -   -   -   -  Glu  -   -   -
Met Ser Gln Ala Glu Phe Asp Lys Ala Ala                            10
ATG TCT CAG GCT GAG TTT GAC AAA GCT GCT                           154
--- --- --- --- --- --- --G --- --- --A

-   -   -  Arg  -   -   -   -   -   -
Glu Glu Val Lys His Leu Lys Thr Lys Pro                            20
GAG GAA GTT AAG CAT CTT AAG ACC AAG CCA                           184
--- --G --- -G- --C --- --- --- --- ---

Ser  -   -   -   -   -   -   -   -  Gly
Ala Asp Glu Glu Met Leu Phe Ile Tyr Ser                            30
GCA GAT GAG GAG ATG CTG TTC ATC TAC AGC                           204
T-G --- --- --- --- --- --- --- --T G--

-   -   -   -   -   -   -   -   -   -
His Tyr Lys Gln Ala Thr Val Gly Asp Ile                            40
CAC TAC AAA CAA GCA ACT GTG GGT GAC ATA                           244
--- --- --- --- --- --- --- --C --- ---

-   -   -   -   -   -   -   -   -   -
Asn Thr Glu Arg Pro Gly Met Leu Asp Phe                            50
AAT ACA GAA CGT CCT GGA ATG TTG GAC TTC                           274
--- --- --- --G --C --G --- --- --- ---

Thr  -   -   -   -   -   -   -   -   -
Lys Gly Lys Ala Lys Trp Asp Ala Trp Asn                            60
AAA GGC AAG GCC AAG TGG GAT GCC TGG AAT                           304
-CG --- --- --- --- --- --- --- --- ---

-   -   -   -   -   -   -   -   -   -
Glu Leu Lys Gly Thr Ser Lys Glu Asp Ala                            70
GAG CTG AAA GGG ACT TCT AAA GAA GAT GCC                           334
--- --- --- --- --- --C --G --- --- ---
```

```
    HindIII
      ↓
    -    -    -    -    -   Asn   -    -    -    -
   Met  Lys  Ala  Tyr  Ile  Asp  Lys  Val  Glu  Glu
   ATG  AAA  GCT  TAC  ATT  GAC  AAA  GTA  GAA  GAA        80
   ---  ---  ---  ---  --C  A--  ---  ---  ---  --G       364

-    -    -    -    -    -    -    *
   Leu  Lys  Lys  Lys  Tyr  Gly  Ile   *
   CTA  AAG  AAA  AAA  TAT  GGA  ATA  TAAGAGACTGAG         87
   ---  ---  ---  ---  --C  --G  ---  -G--------GA       394

TTTGGCTGCCA-GCCATTCATTTCACCTAAACTGATTTA
   -----T-A-TGT-----GTG---AT----------GAC-                434

ATGCCTTGTTTTT--CTAATACTGGGGATGAAGTTCATAA
   --------------TT-------C-T-----GT-GAA 3'               472

ATAACTAGCTAAGCCAGAAGCTCAAGACAGCCCAGGATA                 511

TGACTAACAGATTAGGAGCTGAAACGGTTACTAATCCTT                 550

GCTGAGTAATTTTTATCAGTAGATGAATTAAAAGTATCTT                590

TGTTACTTT/ACTTCG/AT(poly A)-3'                          607
```

VECTORS ENCODING BRAIN DERIVABLE POLYPEPTIDE FACTORS

CROSS REFERENCE TO RELATED APPLICATIONS

This application is a divisional of Application Ser. No. 823,159, filed Jan. 27, 1986, now U.S. Pat. No. 4,963,485 which is continuation-in-part of Application Ser. No. 766,864, filed Aug. 15, 1985, now U.S. Pat. No. 4,806,492, which is a continuation-in-part of Application Ser. No. 694,712, filed Jan. 25, 1985, now U.S. Pat. No. 4,714,683, issued Dec. 22, 1987, which disclosures are incorporated herein by reference.

BACKGROUND OF THE INVENTION

1. Field of the Invention

Cellular growth and differentiation appear to be initiated, promoted, maintained and regulated by a multiplicity of stimulatory, inhibitory and synergistic hormones and factors. The alteration and/or breakdown of the cellular homeostasis mechanism seems to be a basic cause of growth related diseases including neoplasia. There is a considerable interest in the isolation, characterization and mechanism of action of growth modulatory factors (stimulators and inhibitors) because of their potential use in the diagnosis, prognosis and therapy of various diseases, such as cancer, as well as in understanding the basic mechanisms of mitosis, particularly as it may affect cancer.

Besides growth and differentiation, many bodily responses are regulated by proteins, where the proteins may serve as ligands or receptors. Further investigation of the regulation of brain function and response to external and internal stimuli has resulted in the isolation of a myriad of compounds which are involved in the regulation of responses to such stimuli as pain, mood, or the like.

Benzodiazepines (BZD), commonly used as anxiolytics, anticonvulsants, muscle-relaxants and sedatives, are believed to exert their pharmacological effects based on the potentiation of the γ-aminobutyric acid (GABA)-mediated inhibitory neurotransmission. The first step in the modulation of GABA-ergic transmission by BZD appears to be binding to specific high affinity and saturable binding sites in the central nervous system, where the binding sites are believed to be a component of a "supramolecular complex." The need to understand this system, as well as being able to modulate or control the system is dependent on knowing the naturally occurring ligand and the manner in which it functions.

The detection, isolation and purification of these factors is frequently complicated by the complexity of the mixture, the divergencies of activities of the various components in the mixtures, the sensitivity of components to deactivation by a wide variety of reagents, the potential for having compounds which depend for their activity on the presence of multiple subunits, and the frequent difficulties in providing bioassays for tracking various purification steps. Nevertheless, there have been substantial advances in purification and separation, which advances have aided in the detection and isolation of products of interest.

2. Description of the Prior Art

Beal et al., *Cancer Biochem. Biophys.* (1979) 3:93–96 report the presence of peptides in human urine which inhibit growth and DNA synthesis more in transformed cells than in normal cells. Holley et al., *Proc. Natl. Acad. Sci.* (1980) 77:5989–5992 describe the purification of epithelial cell growth inhibitors. Letansky, *Biosci. Rep.* (1982) 2:39–45 report that peptides purified from bovine placenta inhibit tumor growth and thymidine incorporation in DNA to a greater extent in neoplasms than in normal cells. Chen, *Trends Biochem. Sci.* (1982) 7:364–365 reports the isolating of a peptide from ascites fluid with a cancer suppressing property. Redding and Schally, *Proc. Natl. Acad. Sci.* (1982) 79:7014–7018 report isolation of purified peptide(s) from porcine hypothalmi which exhibit antimitogenic activity against several normal and tumor cell lines. Most of these factors have not been fully characterized, nor are their primary structures known.

Diazepam binding inhibitor (DBI) is reported and described by Guidotti, et al., *Proc. Natl. Acad. Sci. USA* (1983) 30:3531–3525, Costa, et al., *Neuropharmacol.* (1984) 23:989–991, Ferrero, et al., ibid (1984) 23:1359–1362, and Alho, et al., *Science* (1985) 229:179–182.

SUMMARY OF THE INVENTION

Novel methods and compositions are provided which compositions are isolatable from brain tissue using acidic aqueous acetonitrile on a gel permeation column followed by reverse phase HPLC employing a linear gradient of acidic (0.1% trifluoroacetic acid) aqueous acetonitrile, as well as the components of such composition and polypeptides having regions of substantial homology with such components. The compositions and components may find use in retarding growth of neoplastic cells, as agonists for diazepam and as surface membrane proteins. Polynucleotide sequences are provided encoding the polypeptides, which allow for production of the polypeptides in prokaryotes or eukaryotes. Antibodies are provided which bind specifically to the subject polypeptides.

BRIEF DESCRIPTION OF THE FIGURES

FIG. 1 depicts the nucleotide sequence and deduced amino acid sequence of a CDNA clone derived from bovine brain (*). Amino acid residues are numbered relative to the proposed initiating methionine. The region homologous to EBZD is overlined by a heavy line, and extended regions of hydrophobic and uncharged amino acids are delineated by lighter lines. Potential glycosylation sites are boxed.

FIG. 2 indicates the human and bovine DNA sequences.

DESCRIPTION OF THE SPECIFIC EMBODIMENTS

Novel compositions are provided comprising combinations of naturally occurring physiologically active polypeptide compounds, the individual polypeptide compounds, physiologically active fragments thereof, and nucleic acid sequences encoding the various polypeptide compounds. The polypeptides have sequences which are homologous or substantially homologous (at least 60% equivalency) to polypeptides found naturally in brain cells of vertebrates, particularly mammals. The compositions have diverse physiological activity and may be specifically localized in brain cells or be found generally in a wide variety of tissues other than brain. The polypeptides are characterized as being isolatable by elution from a chromatographic column employing homogenized brain tissue or purified fraction thereof with an acidic aqueous acetonitrile eluent. One factor can be isolated substantially pure by chromatography using reverse phase HPLC and a slow linear gradient of acidic aqueous acetonitrile. For the other component the desired activity may be further purified using aqueous acidic n-propanol as a linear gradient. The chromatogram may be developed over a period of 4hr or more in order to obtain reasonable separation with flow rates of about 0.1–0.5ml/min. The separation employing the rpHPLC will usually be with a partially purified sample from brain tissue. The partial purification may be conveniently achieved employing gel permeation chromatography with acidic aqueous acetonitrile as the eluent, particularly eluting isocratically. Conveniently, the media may be 40% acetonitrile in 0.1% aqueous trifluoroacetic acid.

The two components have substantially different physiological activities and composition. One factor which will be referred to as endogenous benzodiazepineoid or endozepine (EBZD), shows activity as a valium agonist, binding to diazepam receptors and appears to be a cytoplasmic protein. At low dosage, the EBZD causes agitation and heightened awareness in mammals, while at high dosage, causes sedation. With beating heart cell aggregates, low doses slow the heart beat rate, while high dosages increase the heart beat rate. The compounds show some homology with the sequence published for diazepam binding inhibitor (Guidotti et al., supra).

The peptides are further characterized by having a $K_i$ of about 1–10μM, usually about 3–6μM, in inhibiting the binding of benzodiazepine to brain synaptosomes (see Experimental). The naturally occurring polypeptides will have molecular weights in the range of about 7 to 15kDal, usually 8 to 12kDal, as measured by gel permeation chromatography or 6 to 10kDal with SDS-PAGE (see Experimental). The peptides are hydrophilic. Specific activities can be obtained which exceed 1000 units/mg (see Experimental).

Fragments of EBZD are also bioactive; particularly fragments including amino acids 33 to 52 of EBZD (consensus sequence among different species) have activity as a diazepam binding inhibitor.

The second component is referred to as brain factor (BF) and can be isolated from brain tissue as indicated above. This factor is present in substantially smaller amount than the EBZD and lags EBZD in the gel permeation purification. The compound is found to be effective in inhibiting growth of lung carcinoma cells, as well as inhibiting soft agar colony formation and plating efficiency, all as described in the Experimental section.

BF will generally have a molecular weight of about 5 to 20kDal, usually about 8 to 18kDal, as determined from gel permeation chromatography. The proteins can be purified using rpHPLC and a linear gradient 0.1% TFA aqueous n-propanol eluting at about 20 to 26% n-propanol. The purified protein can have a specific activity of at least about $15 \times 10^3$ units/μg (see Experimental).

A third component may be obtained by using probes which are a pool of oligonucleotides which encode for the amino acid sequence KWDAWN, the amino acids 54 to 59 of hEBZD. The protein is substantially larger than EBZD, has a leader sequence and a stop transfer sequence, so as to be capable of acting as a surface membrane protein, where the major portion of the peptide is external to the cell. This protein is substantially localized in brain tissue.

The proteins may be obtained from any convenient source, particularly vertebrates, more particularly mammals, including bovine, ovine, lagomorpha, murine, primate, particularly human, and the like. The compounds may be used as they occur naturally or may be modified in various ways, such as lacking glycosylation, lacking terminal acylation, particularly acetylation or formylation, employing fragments having physiological activity, such as competitive binding capability to a receptor, e.g., an antibody, having deletions, insertions, being fused to other peptides, being covalently joined to other peptides, e.g., immunogens for antibody formation, or haptens, or being mutated by having one or more, usually not more than about 10 number percent, more usually not more than about 5 number percent, of the amino acids being varied, by insertions, deletions, transitions or transversions.

Each of the polypeptides will now be considered in further detail.

EBZD Polypeptides

The EBZ polypeptides are characterized by being of less than about 20 kilodaltons (kDal), usually less than about 15kDal and will usually be at least about 1kDal, more usually at least about 2kDal.

The polypeptide compositions are further characterized by eluting from a μ-Bondapak-$C_{18}$ column in reverse phase HPLC under ambient conditions employing a linear gradient of 0–60% acetonitrile in 0.1% aqueous trifluoroacetic acid in the range of 28–50% acetonitrile, particularly 29–40% acetonitrile, and more particularly about 29–36% acetonitrile, more specifically 30–34% acetonitrile.

The polypeptides will have at least about 15 amino acids, more usually at least about 20 amino acids, and fewer than about 125 amino acids, usually fewer than about 100 amino acids. The naturally occurring compounds will have a molecular weight in the range of about 7 to 15kDal using PAGE or gel permeation chromatography as described in the Experimental section.

The polypeptide composition will be further characterized by having at least one of the following amino acid sequences, preferably at least two of the following amino acid sequences, and more preferably at least three of the following amino acid sequences, where the sequence may be conserved by the insertion or deletion of up to and including three amino acids or combination thereof.

--- a. Y $aa^e$ $aa^a$ Ar K A T $aa^b$
b. K W D A W
c. A M $aa^c$ A Y $(X)_x$ V E E
d. T K P $aa^d$ $aa^p$ E E M L F I Y $aa^e$ H Y K
e. Q A T V G D I N T E R P G M L D
f. Q A T V G D I N T E R P G M L D F T G K
g. K G T S K E D A

--- wherein:
 $aa^a$ is an aromatic amino acid, particularly phenylalanine and histidine;
 $aa^b$ is any amino acid, particularly an aliphatic amino acid, which may be acidic, basic, or neutral, preferably acidic or neutral of from about 3 to 5 carbon atoms;
 $aa^c$ may be any amino acid, particularly an aliphatic amino acid, which is basic, acidic or neutral, more particularly basic or neutral of from about 5 to 6 carbon atoms;

$aa^d$ is an aliphatic neutral amino acid, which may be polar or non-polar, particularly having an hydroxyl substituent and of from about 3 to 4 carbon atoms;

$aa^e$ is an aliphatic neutral amino acid, which may be polar or non-polar, particularly having an hydroxyl substituent and of from about 2 to 4 carbon atoms;

$aa^p$ is an aliphatic amino acid, which may be neutral polar or acidic, particularly acidic or the amide thereof, and of from 4 to 5 carbon atoms;

Ar is an aromatic amino acid, including tyrosine, phenylalanine, histidine and tryptophan, particularly Y;

$aa^q$ is an aliphatic amino acid, particularly a basic or neutral polar, amino acid of from 4 to 6 carbon atoms, when neutral polar particularly of from 4 to 5 carbon atoms having an amide group, i.e., N and Q, preferably K;

X is from 1 to 3 amino acids, which may be any amino acids, particularly aliphatic amino acids, more particularly having a first neutral amino acid, a second acidic amino acid or amide thereof, and a third basic amino acid; and x is 0 or 1.

For the purposes of the subject invention, the various amino acids will be divided into a number of subclasses. The following Table indicates the subclasses:

|   |   |
|---|---|
| aliphatic | |
| neutral | |
| non-polar | G A P V L I |
| polar | S T C M N Q |
| acidic | D E |
| basic | K R |
| aromatic | F H Y W |

Of particular interest are polypeptides having the above physiological characteristics and including at least one of the following amino acid sequences:

a. TKPaa$^d$DEEMLFIYaa$^e$HYKQATaa$^f$G
b. KWADAWaa$^g$aa$^h$Laa$^i$aa$^j$aa$^k$KEaa$^m$AMaa$^n$AY(X)$_x$VEEaa$^o$KK
c. KQATVGDINTERPGMLDFT wherein:

$aa^d$, $aa^e$, $aa^q$, and Ar are as defined previously;

$aa^f$ is an aliphatic amino acid, which may be neutral or acidic, particularly of from about 4 to 6, more particularly neutral, of from 5 to 6 carbon atoms;

$aa^g$ is an aliphatic neutral amino acid, particularly a polar amino acid of from about 3 to 5, more usually of from 3 to 4 carbon atoms, particularly having an hydroxyl or carboxamido polar substituent;

$aa^h$ is an aliphatic amino acid, which may be neutral or acidic, particularly polar or acidic, having an hydroxyl substituent and of from about 3 to 5 carbon atoms;

$aa^i$ is an aliphatic amino acid, particularly a neutral or basic amino acid, more particularly a non-polar neutral amino acid, of from about 2 to 6 carbon atoms;

$aa^j$ is an aliphatic amino acid, either neutral or acidic, when neutral, preferably non-polar, and particularly of from about 2 to 5, more usually of from 2 to 4 carbon atoms;

$aa^k$ is an aliphatic neutral amino acid, particularly a polar amino acid of from about 3 to 5, more usually of from 4 to 5 carbon atoms, having a chalcogen (oxygen or sulfur) functionality, particularly hydroxyl or methylthio;

$aa^l$ is an aliphatic neutral amino acid, particularly a polar amino acid, having an hydroxyl functionality and of from about 3 to 4 carbon atoms;

$aa^m$ is an aliphatic acidic amino acid of from 4 to 5 carbon atoms;

$aa^n$ is an aliphatic neutral or basic amino acid, of from about 3 to 6 carbon atoms, particularly of from 4 to 6 carbon atoms, where the aliphatic neutral amino acid is preferably non-polar;

$aa^r$ is an aliphatic neutral non-polar or polar amino acid, particularly non-polar of from 3 to 6 carbon atoms, preferably A;

$aa^s$ is an aliphatic neutral non-polar or polar amino acid of from 3 to 4 carbon atoms, when polar, particularly having an hydroxy group, preferably A;

X' is the same as X, usually from 1 to 3 amino acids which are aliphatic amino acids, which may be neutral, acidic or basic, generally of from 4 to 6 carbon atoms, particularly in the order in the N-C direction neutral non-polar, acidic or amide thereof, and basic;

x is 0 or 1; and $aa^o$ is an aliphatic neutral amino acid, which may be polar or non-polar, particularly of from about 4 to 6, usually 5 to 6 carbon atoms, when polar, particularly having a methylthio group.

It being understood, that besides the X, there may be from 1 to 3, preferably 1 to 2, insertions or deletions to maintain the consensus structure between the various members of the family of polypeptides of this invention. Also, the amino acids are the naturally-occurring L-amino acids, although in some instances the D-amino acid may find use.

Compounds of particular interest have the following formula or fragment thereof of at least 10, usually at least 15 and preferably at least 25, amino acids coming within the following sequence, particularly fragments including one of the prior specified sequences:

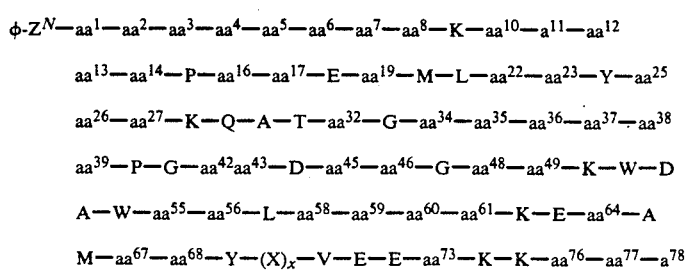

aa⁷⁹—Z^c wherein:
φ is H or acetyl;
$Z^N$ is a bond or from 1 to 10 amino acids, preferably from 1 to 9 amino acids, which may be aliphatic or aromatic, where the sequence is selected from the sequence $$V-H-E-T-R-\begin{matrix}F\\S\end{matrix}-\begin{matrix}E\\Q\end{matrix}-\begin{matrix}A\\E\end{matrix}-,$$

so that any sequence of amino acids within such sequence may be joined to $aa^1$, for example E-A-A or H-E-T-R, or the like, where one may select either amino acid where two amino acids appear at the same site, preferably the amino acids on the same line being taken together;

$aa^{4,8,11}$ are aliphatic neutral non-polar amino acids of from 2 to 6 carbon atoms, particularly glycine, alanine, proline, valine, leucine and isoleucine;

$aa^{5,16,25,35,37,55,60,61,68,73,79}$ are aliphatic neutral non-polar or polar amino acids, where particularly $aa^{5,16,25,35,37,73,79}$ are either, while the remainder are preferably polar amino acids, particularly serine, threonine, cysteine, methionine, asparagine and glutamine;

$aa^{1,6,7,17,19,32,34,38,56,59,64,78}$ are aliphatic neutral amino acids, including polar and non-polar amino acids or aliphatic acidic amino acids, i.e., aspartic and glutamic amino acids; particularly, $aa^{1,7,32,34,59,78}$ are non-polar when neutral amino acids with the remainder being polar when neutral amino acids, and $aa^{1,6,7,17,19,34,38,56,64}$ are preferably acidic amino acids;

$aa^{2,10,13,23,25,26,27,42,43,45,49,77}$ are aliphatic neutral amino acids or aromatic amino acids, particularly phenylalanine, histidine, tyrosine and tryptophan, preferably $aa^{2,10,26,27,45,77}$ are preferably aromatic amino acids, while the remaining amino acids are preferably aliphatic amino acids;

$aa^{3,9,12,14,36,39,46,48,58,67,76}$ are aliphatic neutral or basic amino acids, i.e., lysine and arginine, where $aa^{3,58,67,76}$ are preferably non-polar when other than basic and the remainder are preferably polar when other than basic, except for $aa^{46}$ which may be either polar or non-polar, and $aa^{3,12,14,39,48,58,67,76}$ are preferably basic amino acids;

$aa^{22}$ is basic or aromatic, particularly phenylalanine; X and x have been defined previously; and $Z^C$ is OH, NH$_2$, or a sequence of from 1 to 6, usually 1 to 4 amino acids, particularly aliphatic amino acids of from 2 to 6, usually of from 4 to 6 amino acids, particularly polar or non-polar amino acids, particularly a sequence within the sequence M-P-M-T.

It is understood that one or more of the consensus amino acids may be changed, usually not involving more than two changes, and the consensus sequence may require the insertion or deletion of up to 3, preferably not more than 2, amino acids other than indicated as X.

Polypeptides of interest will have at least 15, preferably at least 30 amino acids in a sequence included in the following sequence:

```
   F E    A V K V I Q S L P K N G
( — —A— — — — — — — — — — — — —
  S Q    E F D K A A E E V K H L
              E                R

S   F Q   T N   M      K F   S
— — )z— — —P— — —E— —M—L— — —Y— —
   K   T K   A D   E      F I   S
                                G

F Y          E   P C K L S K
— — —K—Q—A—T— —G— — — — — — — —
   H F          V   D I N T E R
                       V     D

F W    P V    R Y
P—G— — —D— — —G— — —K—W—D—A—W—
    M L    F K    K A
    L      L T

S S   G D M T      E A   I
— — —L— — — — —K—E— — —M— —A—
  N E   K G T S      D I   K

*  *  *      M    I L E T
Y— — — —V—E—E— —K—K— — — — —
         I D K        L    K Y G I
         V N
         E
``` wherein any amino acid at any site may be substituted for any other amino acid at that site, preferably amino acids above are taken together, while amino acids below are taken together, more preferably amino acids on the same line are taken together, and an asterisk (*) intends a bond (no amino acid at that site), and z is 0 or 1. The sequence may extended by up to a total of 10, usually up to a total of 8, amino acids, where the N-terminus may have the additional sequence V-H-E-T-R or any portion thereof and the C-terminus may have the sequence M-P-M-T, or any portion thereof.

Polypeptides of particular interest include polypeptides having at least about 15, preferably at least about 20, more preferably at least about 30 amino acids, included in one of the following sequences, where such sequences include at least 10, preferably at least 12, and more preferably at least 15 of the amino acids indicated with an asterisk (*) (b=bovine, h=human).

```
                              *
V—H—E—T—R—F—E—A—A—V—K—V—I—Q—S—
       20       *    *    *  *
L—P—K—N—G—S—F—Q—P—T—N—E—M—M—L—

*       *  *  *  *       *
—K—F—Y—S—F—Y—K—Q—A—T—E—G—P—C—K—

—L *  *       *       *     *
—L—S—K—P—G—F—W—D—P—V—G—R—Y—K—

60 *  *  *        *          *  *
—W—D—A—W—S—S—L—G—D—M—T—K—E—E—

*  *    *  *  *  *  *       *  *
—A—M—I—A—Y—V—E—E—M—K—K—I—L—E—T—

—M—P—M—T
```

-continued (bEBZD) S—Q—A—E—F—D—K—A—A—E—E—V—K—
                                    *20
—H—L—K—T—K—P—A—D—E—E—M—L—F—I—Y—
                                              40
S—H—Y—K—Q—A—T—V—G—D—I—N—T—E—R—

—P—G—M—L—D—F—K—G—K—A—K—W—D—A—
      60
—W—N—E—L—K—G—T—S—K—E—D—A—M—K—
                    *80
—A—Y—I—D—K—V—E—E—L—K—K—K—Y—G—I (bEBZD) S—Q—A—E—F—E—K—A—A—E—E—V—R—
                *20                                 *
H—L—K—T—K—P—S—D—E—E—M—L—F—I—Y—
                                              40
G—H—Y—K—Q—A—T—V—G—D—I—N—T—E—R—

—P—G—M—L—D—F—T—G—K—A—K—W—D—A—
      60
W—N—E—L—K—G—T—S—K—E—D—A—M—K—A—
            *80
Y—I—N—K—V—E—E—L—K—K—K—Y—G—I

For particularly preferred compositions of the subject invention, the above sequences may not be changed by having more than about 5 amino acids, inserted, deleted, or substituted, or combinations thereof, preferably not more than about 3 amino acids.

The EBZD compositions will be at least about 20% pure, more usually at least about 30% pure, and preferably at least about 80% pure, more preferably at least about 95% pure, desirably 100% pure. Of particular interest are EBZD compositions which are substantially free of components from source tissue, having less than 1%, preferably less than about 0.1%, and more preferably less than about 0.001% by weight of components from the source tissue. The subject EBZD compositions will have a specific activity of at least 15 units/mg as measured by the amount needed for 40% competition of 3H-diazepam binding to crude synaptosomic membrane under the assay conditions described in the Experimental. Usually, the specific activity will be at least 500 units/mg, preferably at least about 1000 units/mg, and may be 1250 units/mg or higher. Generally, there will be at least about 10μg equivalent per gram of wet tissue in the pineal body, choroid plexus, pons, and optic nerve, and usually at least about 20μg equivalent per gram of wet tissue in the choroid plexus. As indicated previously, the subject compounds will be able to affect heart beat rate in beating heart cell aggregates, slowing the heart beat rate at low doses, generally the low doses being less than about 150μg/ml (see Experimental section). Other characteristics of the EBZD will be evident from the various tests for which physiological activity is demonstrated for EBZD.

Brain Factor

The brain factor is characterized by being at least 2, more usually at least about 5, and not more than about 25, more usually not more than about 22kDal. The brain factor will have a specific activity as evidenced by the cell growth modulatory assay of at least about 1×103, more usually at least about 5×103, preferably at least about $10^6$, preferably at least about $1.5\times10^7$. The brain factor will usually be at least about 10% pure, more usually at least about 50% pure, preferably at least about 80% pure, and more preferably at least about 95% pure, desirably 100% pure. Particularly, it will be desirable that the brain factor be substantially free of components from the tissue from which it is isolated, such as cell debris, other proteins, saccharides, lipids, combinations thereof, and the like.

The brain factor sequence will include a sequence having substantially the following amino acid sequence proximal or at the N-terminus:

N-K-E-L-D-P-V-Q-K-L-F-V-D-K-I-X-E-Y wherein X indicates any amino acid.

The brain factor suppresses human T-cell responses, so as to find use as an immunomodulator for the treatment of hosts with autoimmunity or organ transplants, being used alone or in conjunction with other immunosuppressants, such as cyclosporin A or corticosteroids.

Usually, the brain factor sequence will be at least 65 number percent, preferably at least about 75 number percent homologous to the above sequence (by indicating number percent, it is intended that deletions, insertions, and mutations be counted as additive differences).

The subJect brain factors will also find activity in inhibiting cell growth and inhibiting soft agar colony formation. Thus, the subject compounds find use in inhibiting in vitro and in vivo the multiplication of neoplastic cells, while having substantially less effect on normal cells, usually being able to differentiate by at least one order of magnitude, preferably at least two orders of magnitude between neoplastic and normal cells.

Membrane Protein

The membrane protein will for the most part have the sequence shown in FIG. 1:

The peptides will therefore have at least about 60%, more usually at least about 75%, and preferably at least about 95 number percent of the sequence in FIG. 1. Of particular interest is the sequence underlined with the heavy dark line which has homology with EBZD. The protein is further characterized by being at least about 10% pure, preferably at least about 50% pure, more preferably at least about 80%, and particularly preferred at least about 95% pure, desirably pure. The compound is desirably free of components from the tissue from which it may be derived.

The membrane protein is further characterized by being primarily found in brain tissue.

Additional proteins of interest are included as fragments of the above protein which include polypeptides beginning at the methionine at nucleotide 170 or at nucleotide 270 or 273.

The subject polypeptides may be used as antigens for the production of antibodies, which in turn may be used as antigens for the production of anti-idiotypic antibodies. Either polyclonal or monoclonal antibodies may be prepared in accordance with conventional ways. The subject polypeptides or fragments thereof, generally fragments having at least about 15 amino acids, may be used by themselves, but are preferably bound or linked to an adjuvant or antigen which activates the immune system. Various antigens may be used, such as serum albumins, keyhole limpet hemocyanin, globulins, or the like. A wide variety of techniques are available for linking to polypeptides, such as glutaraldehyde, maleimidobenzoic acid, diazobenzoic acid, or the like. Adjuvants include Freund's adjuvant, aluminum hydroxide, or the like. The antigen is injected into an appropriate host in conventional amounts, where one or more booster injections may be made in from 2 to 4 week intervals. Where monoclonal antibodies are employed, normally a mouse is injected with the original and booster injections and the spleen isolated and the splenocytes fused with an appropriate fusion partner in accordance with conventional techniques. See, for example, Galfre et al., *Nature* (1977) 266:550; Kennett et al., *Current Topics in Microbiology and Immunology* (1978) 81:77; U.S. Pat. Nos. 4,381,292 and 4,363,799. However, for special purposes, other mammals may be employed, such as primates, e.g., humans, for production of antibodies having human $F_c$ chains.

The EBZD polypeptides and antibodies which bind specifically to the EBZD polypeptides may find use individually or together, both in vivo and in vitro. The subject compounds may be used as agonists for binding to diazepam receptors. The subject compounds may be used to determine the number and distribution of diazepam receptors. In addition, the subject compounds may find use in regulating the heart beat of a mammalian host, for sedating a mammalian host or for causing agitation in a mammalian host.

The brain factor polypeptides and antibodies which bind specifically to the brain factor polypeptides may find use individually or together, both in vivo and in vitro. Because of the tumor-inhibiting property of the polypeptides, the polypeptides may be used with mixtures of cells, including both normal and tumorigenic cells, to inhibit the overgrowth of the tumorigenic cells. The subject compounds can therefore be employed in such situations as when mutagenizing normal cells, where one wishes to distinguish between the differences occurring with normal cells and tumorigenic cells as a result of mutagenesis; inhibiting growth of tumorigenic cells where bone marrow has been removed from a mammalian host; detecting binding sites for the subject polypeptides in a cell population; and the like. The brain factor polypeptides may be used for distinguishing or removing T-cells from other cells.

The brain factor polypeptides may be used in vivo for inhibiting tumor cell growth, by injection into tumors, encapsulation into liposomes, where the liposomes may be bound to antibodies specific for or preferential for tumor cells, or the like. Alternatively, the subject polypeptides may be used as immunomodulators.

The polypeptides may be used by themselves or in combination with the antibodies in diagnosis for the polypeptides. Either or both may be labeled or unlabeled for use in diagnostic assays. A large number of diagnostic assays are described in the literature and include the binding, either directly or indirectly, to the subject polypeptides or antibodies of a variety of labels, such as enzymes, radionuclides, fluorescers, substrates, coenzymes, particles, e.g., magnetic particles, or the like. As illustrative of these assays, see for example, U.S. Pat. Nos. 3,817,837; 3,850,752; 4,174,384; 4,277,437 and 4,374,925.

Various assays are divided arbitrarily into homogeneous and heterogeneous immunoassays, where the distinction is based on whether the complex between the polypeptide and its antibody must be separated from the uncomplexed members of the specific binding pair. Various assays are referred to as EIA, ELISA, RIA, homogeneous EIA, dot-blot, Westerns, or the like.

Antibodies to the subject polypeptides may be used in themselves as antigens to produce anti-idiotypes, which may serve as competitive antigens, having epitopic sites competitive with epitopic sites of the subject polypeptides. These anti-idiotypes may therefore serve as diazepam agonists, tumor inhibitors as substitutes for the subject polypeptides or as antagonists for the subject polypeptides.

The above described polypeptides form families of naturally occurring polypeptides which may be derived from natural sources, as well as non-naturally occurring polypeptides which share physiological properties, such as binding specificity, e.g., diazepam receptor and tumor cell inhibition. The naturally occurring compounds may be obtained from naturally occurring sources, primarily brain tissue. However, the subject naturally-occurring compositions may be found in a number of different tissues, such as spleen and testes.

To isolate the subject compounds, brain tissue is freed of blood clots, homogenized, extracted with an organic solvent under acidic conditions ($pH<4$) and then dialyzed to remove low molecular weight material, that is material less than about 4kDal. The resulting product is then freed of compounds which apparently act as inhibitors of its activity using a gel permeation column and an aqueous 0.1% trifluoracetic acid solution- containing from about 35 to 45% acetonitrile eluant. The fractions are monitored by bioassay. The resulting EBZD fraction is further purified employing a reverse phase high pressure liquid chromatographic column, for example, a $\mu$-Bondapak-C18 column employing linear gradients of acetonitrile of from about 0 to 60% in aqueous 0.1% trifluoracetic acid, and using an extended column and slow rates of elution, e.g., greater than 4hr, preferably greater than 5hr. The subject EBZD compounds are found in the fractions of from about 30 to 50% acetonitrile, more particularly from 30 to 40% acetonitrile.

The BF compound containing fraction is further purified using rpHPLC with a linear gradient of 0.1% aqueous acetonitrile, eluting at about 32–36% acetonitrile, with the process being repeated one or more times. This concentrated fraction is then further purified using rpHPLC with a linear gradient of 0.1% aqueous n-propanol, eluting at about 22–24%- n-propanol, with this process being repeated one or more times.

Alternatively, the subject polypeptides may be synthesized in accordance with known techniques, particularly where the polypeptides are fewer than 30 amino acids, more particularly fewer than 25 amino acids. See, for example, Barany and Merrifield, *Solid-Phase Peptide Synthesis,* "The Peptides, Analysis Synthesis Biology," Special Methods in Peptide Synthesis, Part A, Vol. 2, Gross and Merenhofer, eds., Academic Press, N.Y. 1980, pp. 1–284.

For relatively large polypeptides, particularly those of about 20 amino acids or greater, more particularly of about 30 amino acids, hybrid DNA technology may be employed for obtaining sequences encoding for the polypeptide, which may then be used for expression of the desired polypeptide in accordance with known ways. Genomic DNA, cDNA, synthetic DNA or combinations thereof may be employed for coding for the polypeptides, the presence of any introns being accommodated by employing a host cell having a functioning splicing system for the introns. For the most part, an open reading frame will be employed (free of introns), where the sequence coding for the open reading frame will be joined to transcriptional and translational regulatory signals which are functional in the expression host.

cDNAs of particular interest include the CDNAs obtained for EBZDs. The cDNA may include up to about 120bp upstream from the initiating methionine and about 225bp downstream from the translation termination signal, including a poly(A)+tail.

FIG. 2 provides a comparison of nucleotide and deduced amino acid sequences of bovine and human EBZD. Residues that differ in the human sequence are indicated above and below the bovine sequence, which was determined from three overlapping cDNA clones. Nucleotide residues are numbered relative to the composite sequence of the bovine clones; amino acid residues are numbered relative to the initiating methionine. The open reading frame of the bovine sequence is flanked by asterisks (*). Differences in the poly(A)+addition sites of three separate clones are indicated by an inverted slash. The NaeI and HindIII restriction sites used for preparing the bovine cDNA probe are indicated.

The sequences provided in the experimental section, or fragments thereof, fragments having at least about 45 bases (15 codons or greater) may be employed for expression of polypeptides of the subject invention. By employing in vitro mutagenesis, mutagenesis, adaptors or the like, the sequences can be varied from the naturally-occurring sequence to produce sequences having silent mutations or codons that code for non-wild type amino acids. Thus, one can produce both naturally-occurring polypeptides and polypeptides having analogous physiological properties but differing in one or more amino acids.

The coding sequence which is employed may have blunt or cohesive ends for joining to other sequences. For expression, a large number of expression vectors are either commercially available or have been described in the literature. Thus, one can introduce the subject sequence into an expression vector for expression in an appropriate host. The hosts may be prokaryotic or eukaryotic, that is, bacteria, algae, fungi, e.g., yeasts, mammalian cells, e.g., mouse cells, hamster cells, monkey cells, or the like. The expression vector, whether completely assembled for insertion of the coding sequence or assembled in conjunction with the coding sequence for a polypeptide of the subject invention, will be characterized for the most part as follows. Usually, but not always, a replication system other than the wild-type replication system will be available, providing for a low or high copy number of an episomal element to be maintained in the host. Where integration of the coding sequence into the host genome is desired, the replication system will not be required. The coding sequence will be flanked at the 5' and 3' ends by transcriptional and translational initiation and termination regulatory signals respectively, frequently other than the wild-type regulatory regions. Therefore, promoter regions will be employed at the 5' end, which may include capping sequences, operators for regulated expression, the absence of promoter regulation for constitutive expression, enhancer sequences, and the like. At the 3' terminus will be a terminator, stop codons, optimally a polyadenylation sequence, and the like. The expression construct of the transcriptional and translational regulatory sequences and coding sequence will frequently be joined to one or more markers which allow for selection both as to the transformed hosts into which the vector has been introduced and providing for a competitive advantage for those cells which retain the expression vector. Markers may include complementation by providing prototrophy to an auxotrophic host, biocide resistance, such as resistance to various antibiotics, heavy metals, or the like, immunity, etc. The various sequences will be selected so as to be functional in the host.

With many expression vectors, a polylinker is present between the transcriptional and translational initiation and termination regulatory sequences which provide for a plurality of restriction sites. Thus, by appropriate design of the coding sequence or the use of adaptors, the coding sequence may be inserted into the polylinker region.

In certain situations, it may be desirable to join the coding sequence to a 5'-coding sequence so as to obtain a fused product, where the 5'-sequence codes for a leader sequence, particularly for a secretory leader sequence and processing signal. Various secretory leaders have been described in the literature; see, for example, U.S. Pat. No. 4,411,994, EPA 88,632 and 116,201. The coding sequence is joined in proper reading frame to the secretory leader and processing signal, whereby the fused coding sequence may then be inserted into the expression vector to provide for the expression construct.

Where the polypeptide is retained intracellularly, after growing the cells, the cells may be harvested and lysed and the polypeptide isolated. Where the polypeptide is secreted, the nutrient medium may be continuously exchanged and the polypeptide isolated. Various techniques exist for isolation and purification of polypeptides, such as affinity chromatography, HPLC, electrophoresis, gradient centrifugation, solvent extraction, and the like.

Depending upon the use, the subject compounds may be formulated in a variety of ways. For in vivo administration, the subject compounds may be introduced into a physiologically acceptable carrier, such as sterile water, saline, phosphate-buffered saline, ethanol, etc. The concentrations will vary widely depending upon the particular application, whether the application is localized or general, or the like. Administration may be parenterally, intravenously, intraperitoneally, intraarterially, subcutaneously, etc.

For the naturally occurring EBZDs, concentrations will generally be from about 5 to 500µg/mL. Depending upon the manner of administration, dosages may vary from about 0.5 to 500µg/kg, more usually from about 5 to 50µg/kg, with doses exceeding about 25µg/kg having tranquilizing effects. The particular dosage will vary with the desired response, the manner of administration, the repetitive nature of the dosages, and the like.

The following examples are offered by way of illustration and not by way of limitation.

EXPERIMENTAL

Materials and Methods

Materials

Bio-Sil TSK-250 gel filtration HPLC columns were purchased from Bio-Rad Laboratories, Richmond, CA. µ-Bondapak-C18 columns were bought from Waters Associates, Milford, MA. Trypsin (TPCK treated), chymotrypsin and *Staphylococcol aureus* V8 protease were from Worthington. The endoproteinase Lys-C was from Boehringer-Mannheim. $^3$H-labeled diazepam, R015-1788, flunitrazepam, and $\beta$-carboline were obtained from NEN, Boston, MA. Carrier free $^{125}$I-iodine was from Amersham, Arlington Heights, IL.

Purification of Endo-benzodiazepineoid (EBZD) from Bovine Brain

Fresh or frozen bovine brain (480g wet weight) was thawed and minced. The minced tissue was suspended in 2400ml and extraction buffer consisting of 2379ml ethanol (98%), 18.5ml concentrated HCl, 84mg phenylmethylsulfonyl fluoride and 2.5ml of aprotinin [23 TIU/ml from bovine lung (Sigma Chemical Co.)]. The mixture was homogenized in a Waring commercial blender. The homogenate was stirred at 4° C. overnight, centrifuged at 8,000rpm in a Beckman type 19 rotor for 30min, and the supernatant carefully removed. The final volume was about 2070ml. Chloroform (2070ml) and 207ml of acidified water (203ml water and 4ml concentrated HCl) was added to the supernatant, the mixture stirred vigorously for approximately 1h, and allowed to stand at room temperature to separate into two phases. The upper aqueous phase was carefully removed and dialyzed against 20 liters $\times$ 2 changes of 0.1M acetic acid at 4° C. in a Spectrapor dialysis membrane tubing (cutoff 3,500MW, American Scientific Products). The dialyzed supernatant was lyophilized. The lyophilized material (785mg) was termed crude fraction.

Gel Permeation Chromatography

A Bio-Sil TSK-250 column (60$\times$2.1 cm) was attached to a high pressure liquid chromatography (HPLC) system (Waters Associates). The crude fraction was dissolved in 40% acetonitrile in water with 0.1% trifluoroacetic acid at a concentration of 8mg/ml. The column was equilibrated with 40% acetonitrile with 0.1% trifluoroacetic acid (TFA). A 2ml aliquot (16mg protein) was injected and elution was performed isocratically with a mobile phase of 40% acetonitrile in water with 0.1% TFA concentration. The flow rate was set at 2ml/min and the chart speed was set at 0.25cm/min. The chromatography was performed at room temperature. Five ml fractions were collected. Aliquots of each fraction were lyophilized and assayed in triplicate for benzodiazepine (BZD) binding competing activity (BZD-BCA) and growth inhibitory activity.

Once the position of the BZD-BCA was known, (fraction 24) 49 chromatographic runs as described above were made. The active fractions for all runs were pooled and lyophilized. About 65mg active of dried powdered was obtained. This was called the TSK-250 fraction. It contained about 936 units of BZD-BCA activity.

Reverse Phase High Pressure Liquid Chromatography (HPLC) of TSK-250 Fraction

TSK-250 fraction was dissolved (2mg/ml) in 0.1% TFA and further fractionated by reverse phase HPLC using a $\mu$-Bondapak-$C_{18}$ column (78mm i.d.$\times$30cm) at room temperature. The sample was applied isocratically and the column was washed and equilibrated with 0.1% TFA. The flow rate was set at 2ml/min and the chart speed was 0.25cm/min. Linear gradients were used between the primary solvent 0.1% TFA and the secondary solvent acetonitrile in 0.1% TFA. The gradient conditions were 0–28% in 20min., then 28–42% in 140min, 42–52% in 10 min, and then 52–100% in 6 min. All solvents were HPLC grade. Four ml fractions were collected. Aliquots of each fraction were lyophilized and assayed in triplicate for BZD-BCA. Most of the activity eluted between 31–32% acetonitrile concentration.

Fractions 36 and 37 were pooled and diluted with 12ml of 0.1% TFA. The mixture was applied isocratically on a $\mu$-Bondapak-$C_{18}$ column (3.9mm i.d.$\times$30cm) at room temperature. The flow rate was 1ml/min and the chart speed was 0.25cm/min. Again, linear gradients were used between the primary solvent 0.1% TFA and the secondary solvent acetonotrile with 0.1% TFA. The gradient conditions were as follows: 0–30% in 10min, then 30–40% in 60min. Fractions were collected. Almost all of the activity (about 850 units) was eluted in fraction 6 at ~31% acetonitrile concentration. This fraction was called HPLC-C18 fraction and had about 680$\mu$g protein.

Human EBZD was also purified substantially following the above described procedure with human brain tissue.

Preparation of Brain Synaptosome

Crude synaptic membrane fractions were prepared either from the brain of Sprague-Dawley rats weighing ~200g or fresh bovine brain cortex as described by Zuckin, et al., *Proc. Natl. Acad. Sci.* USA (1974) 71:4802–4806. The synaptic membranes were washed three times with 50mM Tris-HCl, pH 7.4 by repeated suspending in the buffer and pelleting by centrifugation. The washed synaptosomal membranes were suspended in 50mM Tris-HCl, ph 7.4 and stored at $-20°$ C.

Assay for EBZD-Binding Competing Activity

The inhibition of the binding of $^3$H-BZD to the washed synaptosome by various fractions or purified protein was used as an indicator of binding competing activity. The binding of $^3$H-BZD to synaptosomal membranes was performed in duplicate in 12$\times$75mm disposable polypropylene tubes either in the absence or presence of 25$\mu$M $\beta$-carboline. The binding mixture contined 20mM Tris-HCl, pH 7.4, synaptic membrane suspension (70–100$\mu$g protein), as desired various concentrations of test compound, 1–5mM of $^3$H-BZD, and 0.5% final concentration of dimethylsulfoxide in a total volume of 0.1ml. After incubation for 30min at 4° C., 0.7ml of 10% cold polyethylene glycol (PEG 6000) in 0.1M Tris-HCl (pH 7.4) was added to each tube. The suspension was immediately filtered under a vacuum on GF/B filter at 4° C. The filter was washed with 10ml of cold 50mM Tris-HCl (pH 7.4) containing 1mg/ml BSA. The filters were transferred to counting vials and 10ml of Aquassine (NEN) were added to each vial and radioactivity determined using a Beckman $\beta$-counter. The radioactivity bound in the presence of 25$\mu$M $\beta$-carboline (2–8% of total binding) was considered to be nonspecific and data were corrected accordingly. The protein concentrations were determined by the method of Lowry, et al., *J. Biol. Chem.* (1951) 193:265–275 using BSA as a standard.

Polyacrylamide Gel Electrophoresis (PAGE)

A 15cm resolving gel (0.75mm thick) of 15.6% polyacrylamide bis-acrylamide (30:0.8) containing 0.1M sodium phosphate, pH7.2, 0.1% SDS and 6M urea was used. The gel contained 10μl TEMED (Bio-Rad) per 20ml of gel and was polymerized by using 1.0μl/ml gel of 20% ammonium persulfate. An upper gel of a 3.5% acrylamide solution using buffer conditions identical to those of resolving gel was poured on top of the lower gel. The comb was inserted into the top gel, leaving about 3mm of upper gel. Forty μl of samples in 0.01M sodium phosphate pH 7.2, 7M urea, 1% SDS and 1% 2-mercaptoethanol, were boiled for 2min and quickly applied. The running buffer was 0.1M sodium phosphate, pH 7.2 containing 0.1% SDS. The gel was run at 5V/cm at room temperature until the tracking dye reached the bottom of the gel. The gel was fixed in 50% methanol and 9% acetic acid, stained with 0.1% Coomasie blue in the fixing solution, and destained with 50% methanol and 9% acetic acid. Following destaining, the gel was dried.

The PAGE method of Laemmli, *Nature* (1970) 227:680-685 was also used employing 15% resolving and 5% stacking gels. Protein on the gels was detected either by the silver staining method of Merril, et al., *Science* (1981) 211:1437-1439, or by Coomasie blue staining.

Iodination of Proteins

Proteins were labeled with $^{125}I$ using the chloramine-T method as described by Barridge, *Methods Enzymol.* (1978) 50:54-65, or by using $^{125}I$-Bolton and Hunter reagent, *Biochem. J.* (1973) 133:529-539.

Antibody Production Against EBZD

Antisera to the purified EBZD from bovine brain were prepared in rats. Six-week-old Sprague-Dawley rats were primed with a total of 20μg of purified protein emulsified in Freund's complete adjuvant. Subsequent booster inoculations were given at two-week intervals using 10μg of protein in Freund's incomplete adjuvant. Test bleeds were taken one week after each inoculation and screened for antibodies using the radioimmunoassay procedure outlined below. Antisera suitable for the assay were generally obtained after only two to three booster inoculations.

Antibody sera was also prepared to the purified bovine brain EBZD in rabbits (New Zealand white weighing approximately 3kg) by a similar method as described for rats except 40μg and 20μg proteins were used, respectively, for the primary inoculation and for the booster injections.

Radioimmunoassay

Purified bovine brain factor was radioiodinated with Chloramine-T to a specific activity of approximately $3 \times 10^{10}$ cpm/μg and stored at 4° C. in TNEN buffer (20mM Tris-HCl, pH 7.4; 5mM EDTA; 150mM NaCl; 0.05% NP40; 0.1% BSA).

For the radioimmunoassay, the following reagents were successively added to polypropylene tubes (3ml capacity): 10μl of purified brain factor standard or sample, 10μl of rat antiserum (diluted 1:30 in TNEN buffer) and 30μl of $^{125}I$-labeled bovine brain factor ($\sim 5 \times 10^4$ cpm). After a 45min incubation at room temperature, 50μl of a 10% suspension of heat-inactivated formalin-fixed *S. aureus* were added and the mixture left for an additional 30min. The immunoabsorbent was then centrifuged (15,000xg, 1min) through a cushion of n-butyl phthalate oil and the amount of radioactivity in the *S. aureus* pellet determined by γ-spectrometry. The radioactivity bound in the absence of antiserum was considered to be nonspecific and data were corrected accordingly.

Tissue to be assayed for RIA reactive material was processed as follows. Fresh or frozen tissue (approximately 1g net weight) was added to 10ml of cold homogenization buffer (20mM Tris-HCl, pH 7.4; 5mM EDTA; 150mM NaCl; 0.2% NP40; 0.2mM phenylmethylsulfonyl fluoride; 100 kallikrein inhibitor units of Trasylol per ml) and homogenized by three 15sec bursts in a Polytron tissue homogenizer. The extract was removed and cleaned of debris by centrifugation for 30min at 100,000xg. The supernatant was then heated to 95° C. for 5min and centrifuged at low speed to remove precipitated protein. Serial 1:3 dilutions of the extract were made in TNEN buffer and used in the radioimmunoassay. A standard curve was included with each set of assays and the amount of immunological reactive material estimated by direct comparison.

Peptide Cleavage by Various Proteases and Isolation of Peptide Fragments.

Bovine and human EBZD were digested in 40μg of 0.1M Tris-acetate, pH 8.0, with the endoproteinase Lys-C for 16h at 24° C. The ratio of EBZD to the enzyme was 10:1 on weight basis. The peptide fragments were separated by rpHPLC on a μ-Bondapak-$C_{18}$ column (Waters) using a linear 2h gradient from 0.05% TFA in water to 60% acetonitrile containing 0.045% TFA. The peptides were monitored and identified by their absorption at 214 nm, collected, lyophilized, and used for the assays.

RESULTS

Purification and Certain Characteristics of Bovine Brain EBZD

The elution profile of EBZD of bovine brain from a column of Bio-Sil TSK-250 was determined. The BZD binding competing activity emerged from the column as a single peak with a median size slightly smaller than ribonuclease (Mr-11,500). The result of chromatography of active fraction 24 from the TSK-250 column on a preparative reverse phase column was that the activity eluted between 31-32% of acetonitrile. Rechromatography of pooled fractions 36 and 37 on an analytical reverse phase column resulted in the elution of active protein as a symmetrical peak. The purification is summarized in Table 1.

TABLE 1

| | Purification of Bovine Brain EBZD | | | |
|---|---|---|---|---|
| Fraction | Weight (mg) | Units[a] | Specific activity (units/mg) | Yield (%) |
| Crude | 785[b] | 1,010[d] | 1.29 | 100 |
| TSK-250 (fraction 24) | 65[c] | 936 | 14.4 | 92.7 |
| HPLC-$C_{18}$ | 0.68[c] | 850 | 1,250 | 84.2 |

[a]Material needed for 40% competion of $^3$H-diazepam binding to crude synaptosomic membrane under the assay condition described above.
[b]Pooled material weighed directly.
[c]Calculated from absorption at 280 nm.
[d]Due to low specific activity, it was not possible to assay directly at this stage. This number indicating total units recovered after TSK-250 chromatography in fractions 24 and 25.

A 969-fold purification with 84.2% yield was achieved in the three-step process. The degree of inhibition increased with increasing concentration of protein. However, the maximum inhibition was found to be only 52% even at 8μM concentration of pure protein. The $K_i$ values were found to be about 5μM, whether $^3$H-diazepam or $^8$H-R015-1788 was used as a ligand.

The homogeneity of the purified protein was demonstrated by PAGE in the presence of 6M urea. The molecular weight of the peptide was estimated to be 10.5kDal. The analysis of the purified proteins (bovine or human) by SDS-PAGE method of Laemmli also gave a single band with an apparent $M_r$~7kDal. The purified proteins emerged as a single symmetrical peak from Bio-Sil TSK-250 column (60cm×7.5mm i.d.) using 40% acetonitrile in water with 0.1% TFA as eluting solvent. The apparent molecular weight was calculated to be about 11.5kDal by this gel permeation chromatography method. The purified human brain EBZD exhibited similar physicochemical and biological properties.

Specific binding of $^{125}$I-labeled (either by Chloramine-T method or by Bolton and Hunter method) purified protein to the synaptosomal membrane was not observed.

Distribution of EBZD

An RIA system was developed to quantitate EBZD in tissue extract, body fluids, and tissue culture cells. The displacement of $^{125}$I-labeled EBZD from bovine brain bound to rat antiserum against bovine EBZD by various peptides was determined. Bovine and human EBZD exhibited a similar potency in competing with $^{125}$I-labeled bovine EBZD bound to rat antiserum prepared to the bovine EBZD protein indicating the presence of quite similar immunogenic determinant(s) in both proteins. None of the peptide fragments of bovine EBZD obtained by endoproteinase Lys-C digestion and purified by reverse phase HPLC showed any immunoreactivity. Thus, the immunogenic determinant of EBZD is not retained on any of the single peptide fragments generated by endoproteinase Lys-C. The distribution of EBZD in various tissues of rabbit is presented in Table 2.

TABLE 2

Distribution of EBZD in Various Rabbit Tissues

| Tissue | μg Equivalent/g Wet Tissue |
| --- | --- |
| Brain | 3.80 |
| Kidney | 3.42 |
| Salivary Gland | 1.76 |
| Liver | 1.52 |
| Stomach | 1.27 |
| Colon | 1.05 |
| Spleen | 0.97 |
| Lung | 0.84 |
| Heart | 0.73 |
| Thymus | 0.67 |
| Pancreas | 0.50 |
| Thigh Muscle | 0.37 |
| Thyroid | 0.06 |
| Serum or Plasma | N.D. |

N.D. = Not detectable.
The details of RIA methods are given previously.

All the tissues tested except serum or plasma contained EBZD as detected by RIA. Bovine brain, spleen, and thymus contained about 11.5, 7.6, and 6.8 μg equivalent per g wet tissue, while human brain was found to contain about 15.7 μg equivalent per g wet tissue. The concentration of EBZD in rabbit brain was found to be much lower than that present in bovine or human brain. EBZD was also found in monkey brain. The antiserum against bovine protein barely detected immunologically cross reacting material in rat and mouse brain. EBZD was also found to be present in human cerebrospinal fluid and ascites fluid. Human breast carcinoma cells (MCF7), liver carcinoma cells (HEP2), neuroblastoma cells (MTB14), glioneuroblastoma cells (CCL127), and glioblastoma cells (HTB10) were estimated to contain 9.1, 8.9, 8.6, 0.32, and 0.26 μg equivalent of EBZD per ml packed cells (~$10^9$ cells). One μg of EBZD contains about $6 \times 10^{13}$ molecules. Thus, MCF7, HEP2, and HTB14 cells contain ~$5 \times 10^5$ molecules of EBZD per cell. Thus, EBZD is widely distributed in mammalian tissues and unlike DBI is not a brain specific peptide. The wide tissue distribution would suggest a general rather than a tissue specific function for EBZD.

TABLE 3

Distribution of EBZD in Various Regions of Rabbit Brain

| Tissue | μg Equivalent/g Wet Tissue |
| --- | --- |
| Cerebrum | 3.4 |
| Cerebellum | 7.5 |
| Medulla Oblongata | 5.3 |
| Pituitary | 1.3 |
| Plfactory Bulb | 2.6 |
| Pineal Body | 17.4 |
| Choroid Plexus | 26.7 |
| Pons | 14.3 |
| Vega Nerve | 1.7 |
| Optic Nerve | 16.2 |
| Olfactory Tract | 8.3 |

The EBZD concentrations were determined by RIA as described previously.

Table 3 summarizes the distribution of EBZD in various regions of rabbit brain as determined by RIA. All regions of brain possess EBZD-like material, however, substantial regional variation in EBZD concentration was noted. The highest amount was found in choroid plexus, and the lowest in pituitary among all the rabbit brain regions tested.

EBZD Analeptic Activity

Male New Zealand rabbits weighing between 2.3-2.6kg were used throughout this study. Icv injections were made by the direct puncture method as described by Jacob et al., *Neuropharmacol.* (1972) 11:1-16 but using slightly different coordinates. The animals are prepared 2 days prior to the experiment by drilling a small hole (0.8mm diameter) in the skull (under pentobarbital anesthesia). The hole is located 1.0mm lateral to the midline and 1.0mm rostral to the bregma. On the day of the experiment, just prior to the injections, local anesthetic is sprayed on the skin wound. A #26 needle is inserted vertically to the depth of 12mm from the surface of the skull. Proper positioning is indicated by the appearance of cerebral spinal fluid. The needle is withdrawn, filled with drug solution, and reinserted to the same depth. Injections are always in a volume of 10μl over a 30-60sec period and made with a syringe microburet. Controls consisted of animals given the same volume of sterile saline. All drugs were dissolved in sterile isotonic saline, and are expressed as their free base.

The animals are generally placed in stanchions 2-3hr prior to the experiment. Colonic temperatures are measured by rectal thermister probes connected to a YSI Scanning Telethermometer which is specially wired to record onto a Leeds-Northrup Speedomax recorder. The experiments are carried out in a constant temperature room of 22.0±1.0° C.

Analeptic activity is indicated by a shortened time of recovery of the righting reflex. Rabbits given 25mg/kg iv of pentobarbital undergo anesthesia during which time it is possible to place them on their backs without having them flip back to the normal upright position. The time at which they could no longer be maintained on their backs was considered as the recovery time of the righting reflex.

Behavior was evaluated by gross observation of various parameters, including pupillary dilation, increased motor activity, increased respiratory rate, etc. In addition, certain stereotypic responses, such as compulsive gnawing or scratching, were carefully observed.

bEBZD

10μg

10min after injection animal starts continuous chewing response. Respiration increased from 90/min to 204/min. Increase in motor activity. No hyperreactivity. No analgesia.

100μg

10min after injection respiration decreased from 98/min to 65/min. Compulsive chewing, and mild excitation. Excitation was short-lasting. No hyperreactivity. No analgesia.

200μg

4min after injection animal closes its eyes. Decreased respiration (108/min to 56/min). Loss of righting reflex 10min after injection. Animal was not in deep anesthesia. Righting reflex was regained 28min after bEBZD administration. No analgesia.

Bests Rate Regulation in Cultured Aggregates of Embryonic Heart Cells

Cardiac ventricles from 8 day old chicken embryos were dissociated into single cells and put into rotation culture for 3 days. This method produces small, regular spheres of cells, approximately 150 microns in diameter. Cells within an aggregate are electrically coupled with each other and beat synchronously, with a regular constant rhythm (Myrdal and DeHaan, *J. Cell. Phys.* (1983) 117:319–325). On the basis of electrophysiological characteristics, this preparation resembles adult mammalian Purkinji fibers, the major cardiac conducting system (Myrdal and DeHaan, *The Initiation of the Heartbeat.* Denis Noble, ed. 1975, Oxford University Press, London, p. 7). These aggregates were equilibrated at 24° C. and treated with bEBZD for 24hr. In two separate experiments, the beat rates of aggregates treated at doses of 100μg/ml differed significantly from controls, as follows:

| Experiment 1: (Beat rate measured as seconds/5 interbeat intervals) | | | |
|---|---|---|---|
| | N | MEAN | STDEV | SE MEAN |
| Untreated | 14 | 11.48 | 1.44 | 0.38 |
| Treated | 14 | 7.94 | 2.04 | 0.55 |
| Experiment 2: | | | | |
| | N | MEAN | STDEV | SE MEAN |
| Untreated | 13 | 24.59 | 3.18 | 0.88 |
| Treated | 12 | 19.33 | 2.37 | 0.68 |

In each experiment, by the Student's T test, the treated population differs significantly from the untreated population. The probability that these populations are the same is less than 0.0001 (p=0.0000).

Sequencing

The amino acid sequences of bovine and human EBZD were determined by microsequence analysis of peptides obtained from digests of bEBZD and hEBZD with (a) the endoproteinase Lysine C; (b) chymotrypsin; (c) *Staphylococcal aureus* V8; and (d) cyanogen bromide. The peptide fragments were purified by rpHPLC using volatile solvents. Amino terminally blocked peptides were incubated in 12N HCl at ambient temperature for 16hr. Samples were then dried by lyophilization. The peptides were subjected to automated repetitive Edman degradation in the Model 470A gas phase Protein Sequencer (Applied Biosystems, Inc.). The phenylthiohydantoin amino acids were analyzed by rpHPLC.

Alternatively, the proteins (bovine and human EBZD) or peptides were hydrolyzed with 6N HCl at 105° C. for 16–20h at reduced pressure. The resulting amino acids were converted to the phenylthiocarbamoyl derivatives and analyzed by Pico TAG system (Waters Associates). Phenylthoicarbamoyl amino acids were detected by absorbance at 254nM.

Chemical Structure of EBZD

The amino acid compositions of bEBZD and hEBZD were determined after hydrolysis with 6N HCl using an automatic amino acid analyzer. All common amino acids except cysteine were present in these proteins. The minimal molecular weight calculated from these data is approximately 9,900 in agreement with that established by SDS-PAGE.

No N-terminal amino acid was detected, even when several cycles of Edman degradation were performed, suggesting that the terminal amino groups of bEBZD and hEBZD are blocked. The sequences were determined as described in the Experimental section. The sequences of bEBZD and hEBZD are as follows, with a comparison of the published sequence of DBI:

```
               1        5         10        15        20
b-EBZD   Acyl-S Q A E F D K A A E E V K H L K T K P A
h-EBZD   Acyl-S Q A E F E K A A E E V R H L K T K P S
r-DBI    . . . . . . . . . . . . . . . . . T Q P T 25        30        35        40
b-EBZD   D E E M L F I Y S H Y K Q A T V G D I N
h-EBZD   D E E M L F I Y G H Y K Q A T V G D I N
r-DBI    D E E M L F I Y S H E K Q A T V G D V N 45        50        55        60
b-EBZD   T E R P G M L D F K G K A K W D A W N E
h-EBZD   T E R P G M L D F T G K A K W D A W N E
r-DBI    T D R P G L L D L K G K X I . . . . . .

65        70        75        80
b-EBZD   L K G T S K E D A M K A Y I D K V E E L
h-EBZD   L K G T S K E D A M K A Y I N K V E E L
r-DBI    . . . . . . . . . . M K T Y V E K V E E L 85
b-EBZD   K K K Y G I
h-EBZD   K K K Y G I
r-DBI    K K K Y . .
```

Residues in the hEBZD amino acid sequences which differ from the bEBZD sequences are underlined.

A comparison of the amino acid sequences of hEBZD with the amino acid sequences of bEBZD indicates that human and bovine EBZD may differ from each other by only a few conservative substitutions.

Five of six amino acid substitutions are compatible with a single base change at the DNA level. These results establish that human and bovine EBZDs are highly conserved structurally among different species.

Identification and Characterization of a cDNA Clone for a Factor from Bovine Brain.

Poly (A+) RNA isolated from bovine tissue was used as a template for cDNA synthesis. First strand cDNA synthesis was performed using oligo (dT) and avian myeloblastosis virus (AMV) reverse transcriptase; the second strand was synthesized using *E. coli* RNase H, DNA polymerase I, and DNA ligase (NAD+). The double-stranded cDNA was made blunt-ended by $S_1$ nuclease digestion followed by a fill-in reaction with the large fragment of *E. coli* DNA polymerase I. Terminal deoxynucleotidyl transferase was used to enzymatically add approximately 15 deoxyguanine residues to the 3' ends of the cDNA. This G-tailed cDNA was then size-fractionated on an A-50 column to eliminate both cDNAs smaller than 500 base pairs, as well as unincorporated deoxyguanine residues. Pooled cDNA was then concentrated by ethanol precipitation in the presence of EcoRI digested λgt.10 DNA.

Ligation of the G-tailed cDNA to EcoRI cut λgt.10 was achieved via a novel method utilizing a single-stranded oligonucleotide linker which contained 12 deoxycytosines at the 3' end and a sequence (AATT) complementary to the single-stranded overhang of EcoRI-cleaved DNA at the 5' end. After in vitro packaging of the ligated DNA, recombinant phage were introduced into the *E. coli* strain C600rk$^{-mk+}$Hfl, which undergoes cell lysis when infected by recombinant, but not wild type, phage. DNA from plaques were thereby screened in duplicate using a radiolabeled synthetic oligonucleotide, 17 nucleotides in length, the sequence of which was predicted by 6 consecutive amino acids (KWDAWN) found in the bovine EBZD; due to codon ambiguity, MS1 was synthesized as a 32-fold degenerate pool of oligonucleotides. Screening with MS1 produced a positive clone which was plaque purified and shown to contain a 1.8Kb insert. This insert was subcloned into the plasmid pEMBL and is designated pMP1. After restriction mapping of the insert, appropriate fragments were then further subcloned into strains of M13 and sequenced by the dideoxy method of Sanger and Coulsen.

The cDNA contained in pMP1 included a DNA sequence approximately 300 base pairs from the 5' end of the insert which was nearly identical to a species of MS1. Furthermore, the nucleotide sequence of pMP1 predicted an amino acid sequence similar, but not identical, to that determined for the sequenced bovine EBZD. That these two proteins are closely related is suggested by the striking conservation of amino acid sequence: by deleting three amino acids from the sequenced EBZD, it is possible to align the remaining amino acids with the sequence of pMP1 so that 43% of the amino acids are conserved. In addition, a number of alterations comprise conservative substitutions. (See earlier chart.)

The finding of pMP1 demonstrates that the bovine EBZD is a member of a family of related genes which may encode proteins of similar biological activity. Finally, it should be noted that pMP1 encodes a protein larger than the sequenced bovine brain factor since an open reading frame extends both upstream and downstream from the known terminal amino acids of the latter protein.

Expression of the EBZD Gene

The above procedure was repeated using bovine spleen. The cDNA obtained was a 0.6kbp insert which was cloned into pEMBL to give pEBZD. Sequencing provided a coding sequence having homology to pMP1. The DNA fragment encoding the bovine endozepine (bEBZD) was excised from the cDNA plasmid, EBZD, by a combination of DraI and NaeI digestion. The fragment was purified by gel electrophoresis and inserted into an expression vector, pSM1,2, at the StuI site. The pSM1,2 expressing vector was developed by splicing the replication origin and β-lactamase gene of pBR322 (Bolivar et al., *Gene* (1977) 2:95), the lac promoter and ribosomal binding sites of pTR213 (Roberts et al., *Proc. Natl. Acad. Sci. USA* (1979) 76:760–764) to the i-Z fused gene of pLG300 (Guarente et al., *Cell* (1980) 1 20:543–553). The resulting plasmid can express the foreign gene inserted at the cloning sites such as the StuI site as a fused protein. In this construction the entire coding sequence for EBZD was fused in frame to the DNA encoding the first 21 amino acids of the Cro protein. The plasmid pSB108 has the insert in the right orientation; the plasmid pSB103 has the insert in the wrong orientation; the plasmid pSB125 contains no insert. The *E. coli* HB101 clones harboring various plasmids were grown up to log phase and induced by addition of IPTG to a final concentration of 1mM at 37° C. for 2hr with shaking. The cells were harvested by centrifugation and lysed by the lysozyme-detergent treatment. Basically, the lysate can be divided into supernatant (cytosol) and pellet (inclusion body) and assayed by immunochemical techniques.

The levels of expressed EBZD fused protein were measured by competitive radioimmunoassay. The results indicate that only the *E. coli* clone containing the EBZD expression vector with the insert in the right orientation (pSB108) produces high levels of EBZD polypeptide. Most cro-EBZD was found in the supernatant fraction (cytosol). Only a detectable amount was found in the pellet fraction (inclusion body). On the other hand, no cro-EBZD was detected in the lysate of either the pSB103 or pSB125 clone. It is estimated that 0.5mg of the cro-EBZD was produced by one liter of cell culture after induction by IPTG.

Purification of Brain Factor from Bovine Brain

Gel Permeation Chromatography

A Bio-Sil TSK-250 preparative column (60×2.1 cm) was attached to a high pressure liquid chromatography (HPLC) system (Waters Associates). The crude fraction was dissolved in 40% acetonitrile in water with 0.1% trifluoroacetic acid (TFA) at a concentration of 8mg/ml. The column was equilibrated with 40% acetonitrile with 0.1% TFA. A 2ml aliquot (16mg protein) was injected and elution was performed isocratically with a mobile phase of 40% acetonitrile in water with a final 0.1% TFA concentration. Once the position of BF was known (fraction 23), a few hundred runs as described previously were made. The procedure for monitoring the fractions was the cell growth modulatory assay described below. The apparent molecular weight of the brain factor (GIA) was calculated to be about 18kDal from this permeation chromatography.

Reverse Phase High Pressure Liquid Chromatography of TSK-250 Fractions

TSK-250 fraction 23 from 15 runs were pooled (volume 75ml). The pooled material was diluted two-fold with 0.1% TFA in water. This mixture was injected isocratically on a μ-Bondapak-C18 column (78mm i.d.×300mm) previously equilibrated with 0.1% TFA in water (0.1% TFA) at ambient temperature. Linear gradients were used between the primary solvent 0.1% TFA and the secondary solvent acetonitrile with 0.1% TFA. The gradient conditions were 0–28% in 20min. 28–42% in 140min, 42–52% in 10min, and then 52–100% in 6min. All solvents were HPLC grade. Four ml fractions were collected. Aliquots of each fraction were dried with 50μg BSA and assayed for GIA. Two peaks of GIA were observed. The first activity (α) eluted between 32–33.5% acetonitrile concentration whereas the second peak (β) eluted between 34.5–36% acetonitrile concentration. Further purification of α activity was performed as follows:

Active fractions 30 and 31 from 10 runs were pooled and diluted two-fold with 0.1% TFA. The diluted sample was applied isocratically on μ-Bondapak column (78×300mm) and column was washed and equilibrated with 0.1%TFA. The flow rate was 1ml/min and the chart speed was 0.1cm/min. Again, linear gradients were used between the primary solvent 0.1% TFA and the secondary solvent acetonitrile having a concentration of 0.1% TFA. The gradient conditions were 0–30% in 40min, 30–38% in 240min, and 38–100% in 20min. The first 12 fractions were 6ml and then 4ml fractions were collected. An aliquot was assayed for GIA. The activity eluted between 32–33.5% acetonitrile concentration.

Fractions 30–32 were pooled. Twelve ml of 0.1% TFA were added to the pooled fractions. The mixture (24ml) was isocratically applied onto an analytical μ-Bondapak C18 column (3.9×300mm), equilibrated with 0.1% TFA. The flow rate and chart speed were 0.4ml/min and 0.1cm/min, respectively. Again, linear gradients were used between the primary solvent 0.1% TFA and the secondary solvent acetonitrile having a concentration of 0.1% TFA. The gradient Conditions were 0–30% in 25min, 30–38% in 200min, and 38–100% in 25min. Two ml fractions were collected. An aliquot of the fractions were assayed for GIA. The activity eluted from the analytical C18 column at about 34% acetonitrile concentration.

Fractions 29–31 were pooled and diluted two-fold with 0.1% TFA and applied on a μ-Bondapak C18 column (3.9×300mm). Linear gradients between the primary solvent 0.1% TFA and the secondary solvent n-propanol having a concentration of 0.1% TFA were used. The gradient conditions were 0–18% in 40min, 18–27% in 225min, and 27–35% in 20min. The flow rate was 0.4ml/min and the chart speed was set at 0.1cm/min. Fractions were collected and aliquots assayed for GIA. The activity eluted at about 23% n-propanol concentration.

Fractions 28 and 29 were pooled and diluted five-fold with 0.1% TFA and rechromatographed on a μ-Bondapak C18 column (319×300mm) using n-propano having a concentration of 0.1% TFA as a secondary solvent. The chromatographic and gradient conditions were the same as described immediately above. The first eight fractions were 6ml and then 1.6ml fractions were collected. Aliquots of each fraction were assayed for GIA. Most of the activity appeared in fractions 15 to 17. Fraction 15 to 17 contained about 15μg protein and approximately 230×$10^3$ units of GIA. This fraction was termed HPLC-C18[5] fraction. The final purified fraction had a specific activity of 15.33×$10^3$ units per μg protein using CCL64 as test cells.

The following Table 4 summarizes the results.

TABLE 4

Purification of Bovine Brain Factor

| Fraction | Weight (mg) | Units* (×$10^{-3}$) | Specific Activity (Units/mg × $10^{-3}$) | Yield (%) |
|---|---|---|---|---|
| Crude | 3,680 | 1,551 | 0.421 | 100 |
| TSK-250 | 630 | 2,760 | 4.38 | 181 |
| HPLC-C18[5] | 0.015 | 230 | 15,333.00 | 14.8 |

*Material needed for 50% inhibition of $^{125}$I-deoxy uridine incorporation into DNA of CCL64 cells.

Cell Growth Modulatory Assay Using $^{125}$I-Deoxyuridine Incorporation into DNA The assays were performed in Nunc 96 well plates (Kamstrupvej 90. DK-4,000, Roskilde, Denmark). Human lung carcinoma cells (A549) or mink lung cells (CCL64) were used as test cells. 3.5×$10^3$ cells in 50μl of Dulbecco's modified Eagle's medium (DMEM) with 10% fetal calf serum (FCS) and penicillin/streptomycin (P/S) (0.57mg/ml each) and glutamine were introduced to all wells except peripheral wells. The peripheral wells received 50μl PBS and the plates were incubated at 37° C. The test samples were suspended in DMEM with 10% FCS, P/S, and glutamine for triplicate testing. After 4 hours, 50μl of test samples were added to each test well, while control wells received only 50μl of medium. Plates were incubated at 37° C. for 3 days. On day 4, 100μl of a solution of $^{125}$I-iodo-2'-deoxyuridine [(4Ci/mg–0.5mCi/ml 1.0μ)](1.0μl isotope/ml in DMEM containing 10% FCS, P/S, glutamine) were added to each well and plates incubated at 37° C. On day 5, the medium was aspirated from the wells, washed 1x with 200μl PBS. Then, 200μethanol were added to each well, plates were incubated for 10 minutes and methanol removed by aspiration. Sodium hydroxide (200μl, 1M) was added to each well, the plates were incubated for 30min. at 37° C. and then sodium hydroxide was removed with Titertek plugs (Flow Labs). The plugs were transferred into 12×75mm plastic tubes and counted in a gamma counter in order to quantitate the radioactivity.

Soft Agar Colony Inhibition Assay

A 2.0ml base layer of 0.5% agar (Agar Noble; Difco Laboratories, Detroit, Mich.) in DMEM containing 10% calf serum was added to 60mm Costar tissue culture dishes. A 2.0ml overlay of 0.3% agar containing the same medium-calf serum mixture, 1.0×$10^4$ A549 Ag3 (soft agar growing clone 3 cells and the sample to be tested at various concentrations in duplicate were added. The plates were incubated at 37° C. in a humidified atmosphere of 5% $CO_2$ in air and refed after 7 days by addition of 2.0ml of 0.3% agar containing appropriate supplements. Colonies were measured unfixed, unstained and the number of colonies greater than 6 cells per 5 low power random fields were scored after 7 and 14 days.

Plating Efficiency Assay

The assay was performed in 6 well Falcon plates (9.6cm² area/well). A549 cells (200) were plated in each well in 1ml of DEM with 10% FCD, P/S and glutamide. Immediately following plating, various concentrations of test material in 1.0ml of medium in duplicate were added to wells. The control wells received only 1.0ml of medium without any test material. Plates were incubated at 37° C. in a humidified atmosphere of 5% $CO_2$ in air for 10 days, medium aspirated, 1.0ml of 0.2% methylene blue in 50% methanol was added at each well and allowed to stand for 20min, stain removed, each well washed 2× with 0.1ml water and air dried. The size and number of colonies were quantitated.

Biological Properties

A 50% inhibition of DNA synthesis was observed at 98μg/ml, 21μg/ml and 95ng/ml of crude fraction, TSK-250 fraction and the final pure protein, respectively. Thus, a 50% DNA synthesis inhibition in A549 human lung Carcinoma cell was seen at approximately 9nM concentration of the pure protein.

bBF also inhibited the anchorage independent growth of human carcinoma lung cells A549 on agar (Ag). A 50% reduction in colony formation in soft agar was seen at about 76ng/ml of bBF. The plating efficiency of A549 cells was markedly inhibited by the protein. At 13ng/ml (1.24nM) concentration of protein, the plating efficiency was only 50% compared to that of the control. No colonies of A549 cells were seen in the presence of approximately 80ng/ml bBF.

When A549 cells were grown in the absence and presence of various concentrations of bBF, and cell growth monitored by direct cell count, it was found that bBF inhibited cell growth in a dose dependent manner. Thus, the extent of $^{125}$I-deoxyuridine incorporation into DNA is a good measure of cell growth.

bBF inhibited the growth of various clones of A549 cells, human melanoma cells (A375 Ag) and human breast carcinoma cells (MCF-7). The growth of human foreskin fibroblast (WI-26) was stimulated by bBF. The brain factor was also growth stimulatory to murine fibroblastic cell line 3T3-A31.

Effect on Human T Lymphocyte Proliferative and Cytotoxic Responses to Alloantigens A micromethod for generating and assaying allogeneically induced proliferative and cytotoxic human lymphocytes was used to study the effect of brain factor on human T-cell functions (Zarling et al., *Transplantation* (1976) 21:468–476). Periphera blood lymphocytes (PBL) were isolated from heparinized blood of normal individuals by Ficoll-Hypaque centrifugation. The PBL were then washed 3× with phosphate buffered saline (PBS) and were suspended at a concentration of 1×10$^6$ PBL/ml in RPM1 1640 medium (Gibco, Grand Isle, NY) supplemented with 10% heat-inactivated pooled normal human serum (HS). Then 0.1ml of these PBL (referred to as "responding cells") was added to each of ten replicate round-bottomed wells of 96-well plates followed by the addition of 0.05ml medium alone or 0.05ml medium containing 2×10$^5$ X-irradiated (2500 Rad) allogeneic cells (referred to as "stimulating cells") and 0.05ml medium alone or medium containing various concentrations of brain factor (resulting in 0.9 to 75 unites brain factor/well). The cells were incubated at 37° C. in a 5% $CO_2$ incubator and on days 2 and 5 0.05ml medium was removed from each well followed by the addition of 0.05ml medium containing the original concentration of brain factor.

To determine proliferative responses, on day 6 the contents of wells from each group were pooled and 0.1ml was added to each of four replicate wells of 96-well plates followed by the addition of one μCi $^3$H-thymidine ($^3$H-TdR, New Engand Nuclear, Boston, MA) in a volume of 0.025ml. Six hours later the contents of wells were harvested on glass filter strips using a multiple well harvestor, the strips were transferred to vials containing scintillation fluid, and $^3$H-TdR incorporation was determined by counting in a β counter.

To determine the effect on the generation of cytotoxic T lymphocytes (CTL), the remaining lymphocytes pooled from wells on day 6 were added to three replicate round-bottomed wells of 96-well plates (0.15ml/well) and 0.15ml of serial four-fold dilutions was also added to each of three replicate wells. To prepare $^{51}$Cr labeled target cells, 1.5×10$^6$ lymphoblastoid cell line (LCL) cells, generated from the donors of the allogeneic stimulating cells, were labeled with 500μCi $^{51}$Cr ($Na_2CrO_4$), New England Nuclear, Boston, MA) for 1hr at 37° C. followed by washing the target cells 3× with medium containing 15% heat-inactivated fetal calf serum (FCS) and were resuspended in this medium at cells/ml. Then 0.05ml target cells was added to each well containing effector cells and to wells containing the medium alone (to determine spontaneous $^{51}$Cr release) or detergent alone (to determine $^{51}$Cr release) and the plates were incubated for 6hr at 37° C. Then a constant aliquot of supernatant was removed from each well and transferred to tubes for counting in a gamma counter. The percent specific $^{51}$Cr release was determined as follows:

$$\frac{cpm \text{ experimental release} - cpm \text{ spontaneous release}}{cpm \text{ maximal release} - cpm \text{ spontaneous release}} \times 100$$

The following Table 5 indicates the results:

TABLE 5

| \multicolumn{5}{c}{Effect of Brain Factor on Alloantigen-induced Proliferative Response of Human T-Lymphocytes} |
|---|---|---|---|---|
| Responding Cells | Stimulating Cells | Brain Factor Units/Well | CPM $^3$H-TdR Incorporated | Percent Reduction |
| V | 0 | 0 | 207 | |
| V | Cx | 0 | 103,690 | |
| V | Cx | 75 | 70,140 | 33 |
| V | Cx | 25 | 64,507 | 38 |
| V | Cx | 8 | 78,287 | 25 |
| V | Cx | 2.7 | 87,095 | 16 |
| V | Cx | 0.9 | 99,552 | 4 |

Peripheral blood lymphocytes (PBL) were isolated from heparinized blood of normal individual V and were stimulated with X-irradiated (2500 Rad) allogenic PBL from individual C (Cx); and 6 days later, $^3$H-thymidine ($^3$HTdR) incorporation was determined as detailed above. CPM = counts per minute.
Similar effects of brain factor were observed on T-cell proliferative response of PBL of all other donors tested. A more marked degree of inhibition by brain factor was observed on the generation of human cytotoxic T-lymphocytes.
Approximately 16 times more effector cells incubated with 75 units of brain factor are required to cause 42% $^{51}$Cr release as the number of untreated effector cells to cause this same amount of $^{51}$Cr release.

It is evident from the above results that the subject compounds can be used in a wide variety of ways, both in vitro and in vivo. The subject polypeptides and antibodies can be used diagnostically for determining, intracellularly or extracellularly, in physiological fluids, e.g., blood, serum, plasma, urine, or cerebrospinal fluid, the presence of such polypeptides by recognized diagnostic assays, for determination of the amount of the polypeptide formed by cells in tissue. Also, the subject compounds can be used for the detection of receptors for the polypeptides. In addition, the subject compounds can be used for modulating the rate of growth of tumor cells, both in the presence and absence of normal cells, as immunomodulators or for modifying physiological functions associated with the diazepam receptors or GABA-ergic receptors. Thus, the brain factor compounds derivable from brain tissue and fragments thereof can be used in conjunction with other additives for removing tumor cells from a mixture of normal and tumor cells, such as in bone marrow, tumors, e.g., melanomas, sarcomas, or carcinomas, for surgical or post-surgical treatments, or the like. The brain factor compounds can also be used for modulating the proliferation of T-cells. The EBZD compounds may be used in modulating the activity of the EBZD receptors.

Although the foregoing invention has been described in some detail by way of illustration and example for purposes of clarity of understanding, it will be obvious that certain changes and modifications may be practiced within the scope of the appended claims.

What is claimed is:

1. A DNA expression construct comprising a DNA sequence encoding a first polypeptide sequence having at least one epitopic site cross reactive with a second polypeptide found in mammalian brain capable of specifically binding to the diazepam receptor in vitro, said first polypeptide including substantially the following sequence or a physiologically active fragment of at least about 30 amino acids thereof:

```
F E    A V K V I Q S L P
— —A— — — — — — — — — —
S Q    E F D K A A E E V
         E
              K N GS F Q    T N
              — — — — —P— — —
              K H L K T K    A D
              R              S

M    K F    S F
E— —M—L— — —Y— — —Y—K—Q—A—T—
    E    F I    S H
              G
              E    P C K L S K
              —G— — — — — — —
              V    D I N T E R

F W    P V    R Y
P—G— — — —D— — —G— — —K—W—D—A—W—
    M L    F K    K A
           T
```

-continued
```
              S  S    G D M
              — —L— — — — —
              N  E    K G T
T    E    I        *  *  *
—K—E—  —A—M—  —A—Y— — —  —V—E—E—
S    D    K       I D K
                    N
                    M          I L E T
                    —K—K— — — — —
                    L          K Y G I
``` where plurality of amino acids at a site indicates that any amino acid at that site may be substituted by any other amino acid at that site and an asterisk (*) intends a bond may be employed at that site, said DNA sequence joined in proper orientation to at least one of a promoter other than the wild-type promoter, a terminator other than the wild-type terminator, or a replication system other than the wild-type replication system.

2. A DNA expression construct according to claim 1, wherein said replication system, promoter and terminator are functional in a eukaryotic host.

3. A DNA expression construct comprising a DNA sequence encoding an active polypeptide, said polypeptide characterized by eluting in the 20% to 26% n-propanol fraction in aqueous 0.1M trifluoroacetic acid-n-propanol, being of from about 8 to 18 kDal, inhibiting tumor cell or T-cell growth and being found in mammalian brains, or a physiologically active fragment thereof, said DNA sequence joined in proper orientation to at least one of a promoter other than the wild-type promoter, a terminator other than the wild-type terminator, or a replication system other than the wild-type replication system.

4. A DNA expression construct according to claim 3, wherein said replication system, promoter and terminator are functional in a prokaryotic host.

5. A DNA expression construct comprising a DNA sequence encoding a polypeptide having substantially the same amino acid composition as membrane protein as set forth in FIG. 1 or a fragment thereof, said fragment beginning at methionine 37, 68 or 69, said DNA sequence joined in proper orientation to at least one of a promoter other than the wild-type promoter, a terminator other than the wild-type terminator, or a replication system other than the wild-type replication system.

6. A DNA expression construct according to claim 5, wherein said replication system, promoter and terminator are functional in a prokaryotic host.

* * * * *